US011134970B2

(12) United States Patent
Fiksen et al.

(10) Patent No.: US 11,134,970 B2
(45) Date of Patent: Oct. 5, 2021

(54) FORCEPS KNIFE BLADE LOCKOUT MECHANISM

(71) Applicant: Gyrus ACMI, Inc., Southborough, MA (US)

(72) Inventors: Christian J. Fiksen, Maple Grove, MN (US); Hanam S. Pham, Minneapolis, MN (US); Eric J. Boone, Saint Michael, MN (US); Zane R. Ward, Prior Lake, MN (US)

(73) Assignee: Gyrus Acmi, Inc., Westborough, MA (US)

( * ) Notice: Subject to any disclaimer, the term of this patent is extended or adjusted under 35 U.S.C. 154(b) by 526 days.

(21) Appl. No.: 15/949,254

(22) Filed: Apr. 10, 2018

(65) Prior Publication Data

US 2019/0307473 A1 Oct. 10, 2019

(51) Int. Cl.
    *A61B 17/285* (2006.01)
    *A61B 17/28* (2006.01)
    *A61B 18/14* (2006.01)
    *A61B 18/00* (2006.01)
    *A61B 17/00* (2006.01)

(52) U.S. Cl.
    CPC ........ *A61B 17/285* (2013.01); *A61B 17/2833* (2013.01); *A61B 17/2841* (2013.01); *A61B 18/1445* (2013.01); *A61B 2017/00367* (2013.01); *A61B 2018/0063* (2013.01); (Continued)

(58) Field of Classification Search
    CPC ............... A61B 17/295; A61B 17/285; A61B 2018/00601; A61B 2018/1452; A61B 2018/1455; A61B 2017/320052; A61B 2017/2933; A61B 2017/2936; A61B 17/2833; A61B 2017/2946; A61B 17/2841; A61B 17/2909; A61B 18/1445; A61B 17/29; A61B 18/1442–1447; A61B 2018/145–146; A61B 17/28; A61B 17/2804; A61B 17/2812–282; A61B 2017/2825; A61B 2017/2829; A61B 2017/2837; A61B 2017/2901–2908; A61B 2017/291–2947; A61B 17/068–0686;
    (Continued)

(56) References Cited

U.S. PATENT DOCUMENTS

| 8,968,310 B2 | 3/2015 | Twomey et al. |
| 9,610,116 B2 | 4/2017 | Twomey et al. |

(Continued)

*Primary Examiner* — Katherine H Schwiker
*Assistant Examiner* — Alexis D Amechi
(74) *Attorney, Agent, or Firm* — Schwegman Lundberg & Woessner, P.A.

(57) ABSTRACT

A forceps includes jaws, a first shaft having a first slot, a second shaft extending along the first shaft and having a second slot, and a rod that extends along the second shaft. The rod has a third slot including a locking portion and a guide track portion. A pin extends through the first slot, the second slot, and the third slot to prevent deployment of the rod when the pin is in the locking portion and to permit deployment of the rod when the pin is in the guide track portion. A first actuator produces relative movement of the first and second shafts to move the jaws relative to each other and move the pin from the locking portion to the guide track portion of the third slot. A second actuator produces movement of the rod to deploy the rod when the pin is in the guide track portion.

18 Claims, 8 Drawing Sheets

(52) U.S. Cl.
CPC ............... *A61B 2018/00595* (2013.01); *A61B 2018/1455* (2013.01)

(58) Field of Classification Search
CPC ............ A61B 17/072; A61B 17/07207; A61B 17/07292
See application file for complete search history.

(56) References Cited

U.S. PATENT DOCUMENTS

| | | |
|---|---|---|
| 9,681,883 B2 | 6/2017 | Windgassen et al. |
| 9,717,497 B2 | 8/2017 | Zerkle et al. |
| 2007/0088375 A1* | 4/2007 | Beane .................... A61B 17/11 606/167 |
| 2010/0114137 A1* | 5/2010 | Vidal .................... A61B 17/282 606/167 |
| 2010/0204697 A1* | 8/2010 | Dumbauld ........... A61B 18/085 606/51 |
| 2013/0138102 A1* | 5/2013 | Twomey ............ A61B 18/1445 606/45 |
| 2014/0025071 A1* | 1/2014 | Sims ................. A61B 17/2812 606/46 |
| 2017/0020543 A1* | 1/2017 | Soni ........................ A61B 17/29 |
| 2017/0196579 A1 | 7/2017 | Batchelor et al. |

* cited by examiner

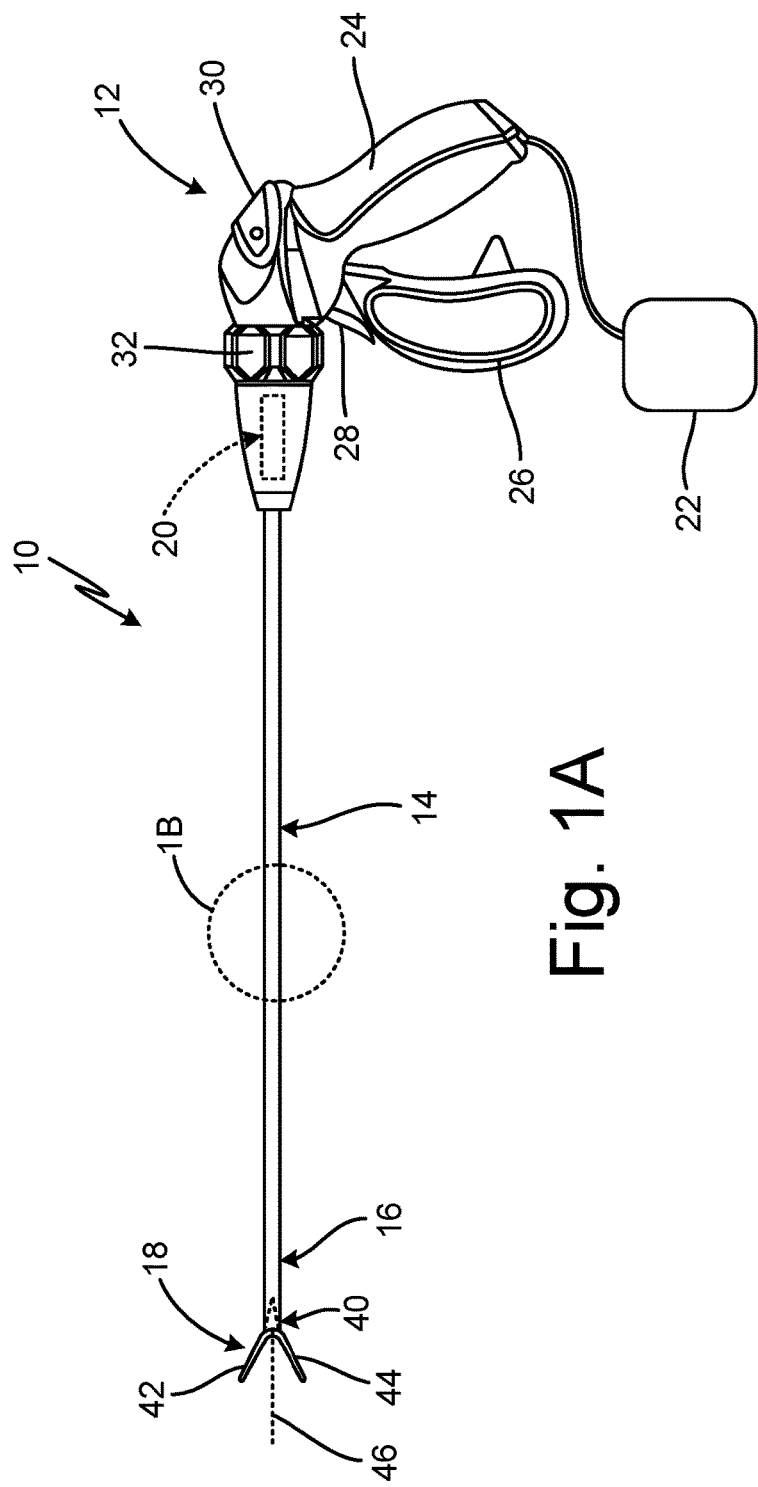
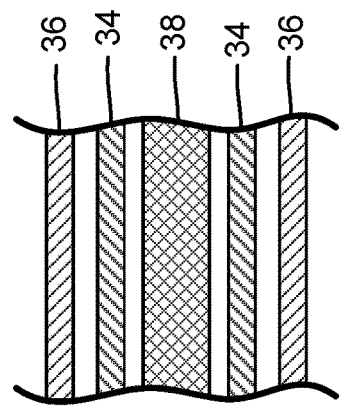

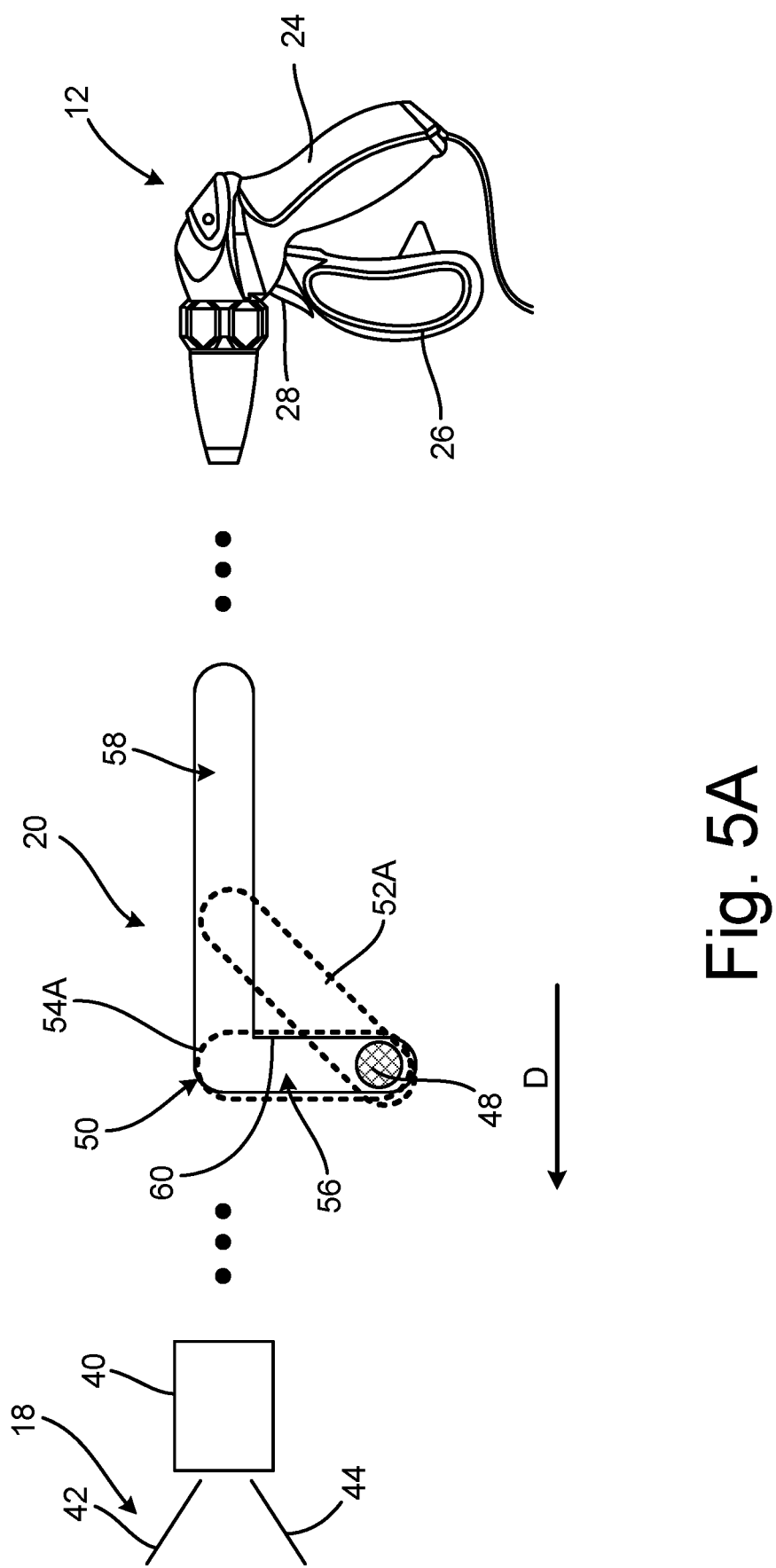

FORCEPS KNIFE BLADE LOCKOUT MECHANISM

BACKGROUND

The present disclosure relates to forceps, and in particular to a knife blade lockout mechanism that prevents deployment of a knife blade to an extended position until a gripping assembly of the forceps is in a closed configuration.

Forceps, such as electrosurgical forceps, are often used for medical procedures, such as laparoscopic surgeries. The forceps can be used to manipulate, engage, grasp, or otherwise affect an anatomical feature, such as a vessel or other tissue. Jaw members of a gripping assembly located at a distal end of the forceps are typically actuated via a lever or other control elements at a hand piece of the forceps to cause the jaw members to move between an open position and a closed position to engage tissue or other anatomical feature therebetween.

Cutting forceps typically include a knife blade assembly that is actuated via control elements at the hand piece, such as a knife blade trigger, to extend and retract a knife blade at the distal end of the forceps to cut or dissect tissue or other anatomical feature(s) engaged between the jaw members. Often, electrosurgical cutting forceps utilize both mechanical clamping action and electrical energy to coagulate, cauterize, seal, desiccate, or otherwise effect hemostasis by heating the tissue or other anatomical feature(s). The knife blade is typically deployed to an extended position to cut or dissect the tissue subsequent to effecting hemostasis, thereby minimizing bleeding of the tissue or other anatomy.

Conventional forceps often utilize a safety knife blade lockout mechanism in the hand piece of the forceps to prevent unintentional extension and/or cutting by the knife blade when the jaw members are open. For instance, certain conventional forceps utilize an interaction between a gripping lever that moves the jaw members and a knife blade trigger that extends and retracts the knife blade to prevent the knife blade from being unintentionally deployed when the jaws are open.

SUMMARY

In one example, a forceps includes jaws that open and close, a first shaft, a second shaft, a rod, a pin, a first actuator, and a second actuator. The first shaft has a first slot. The second shaft extends along the first shaft and has a second slot. The first slot and the second slot are angled with respect to each other. The rod extends along the second shaft and has a third slot including a locking portion and a guide track portion. The pin extends through the first slot, the second slot, and the third slot to prevent deployment of the rod when the pin is located in the locking portion of the third slot and to permit deployment of the rod when the pin is located in the guide track portion of the third slot. The first actuator produces relative movement of the first shaft and the second shaft to move the jaws relative to each other and move the pin within the first slot and the second slot from the locking portion to the guide track portion of the third slot. The second actuator produces movement of the rod to deploy the rod when the pin is located in the guide track portion.

In another example, a method includes producing relative movement of a first shaft and a second shaft to move jaws of a forceps towards a closed configuration. The method further includes moving, during the relative movement of the first shaft and the second shaft, a pin that extends through a first slot in the inner shaft, a second slot in the outer shaft, and a third slot of a rod from a locking portion of the third slot to a guide track portion of the third slot. The method further includes producing movement of the rod relative to the first shaft and the second shaft to deploy the rod when the pin is located in the guide track portion of the third slot.

In another example, a forceps includes a shaft assembly, a gripping assembly, a knife blade assembly, a knife blade lockout mechanism, a gripping actuator, and a knife blade actuator. The shaft assembly has a first shaft and a second shaft. The gripping assembly is operably coupled to a distal end of the shaft assembly and includes a first jaw member and a second jaw member. The knife blade assembly includes a blade support and a knife blade. The blade support extends longitudinally within the shaft assembly. The knife blade is connected to a distal end of the blade support. The knife blade lockout mechanism includes guide slots, cam slots, a blade support slot, and a pin. The guide slots are formed in the first shaft. The cam slots are formed in the second shaft. The blade support slot is formed in the blade support. The blade support slot has a locking portion and a guide track portion. The pin extends through the guide slots, the cam slots, and the blade support slot to prevent distal translation of the blade support and the knife blade when the pin is located in the locking portion and to allow distal translation of the blade support and the knife blade when the pin is located in the guide track portion. The gripping actuator is operably connected to the shaft assembly to produce relative movement of the first shaft and the second shaft that causes at least one of the first jaw member and the second jaw member to transition from an open configuration to a closed configuration and causes the guide slots and the cam slots to move the pin from the locking portion to the guide track portion of the blade support slot. The knife blade actuator is operably connected to the knife blade assembly to produce distal translation of the blade support relative to the first shaft and the second shaft to extend the knife blade when the pin is located in the guide track portion of the blade support slot.

BRIEF DESCRIPTION OF THE DRAWINGS

FIG. 1A is a side view of a forceps having a knife blade lockout mechanism.

FIG. 1B is a cross-sectional view of a portion of the forceps of FIG. 1A.

FIG. 5A is a schematic diagram of the forceps showing a hand piece, gripping assembly, and knife blade lockout mechanism when the gripping assembly is in an open configuration and the knife blade is retracted.

DETAILED DESCRIPTION

Figure 2:
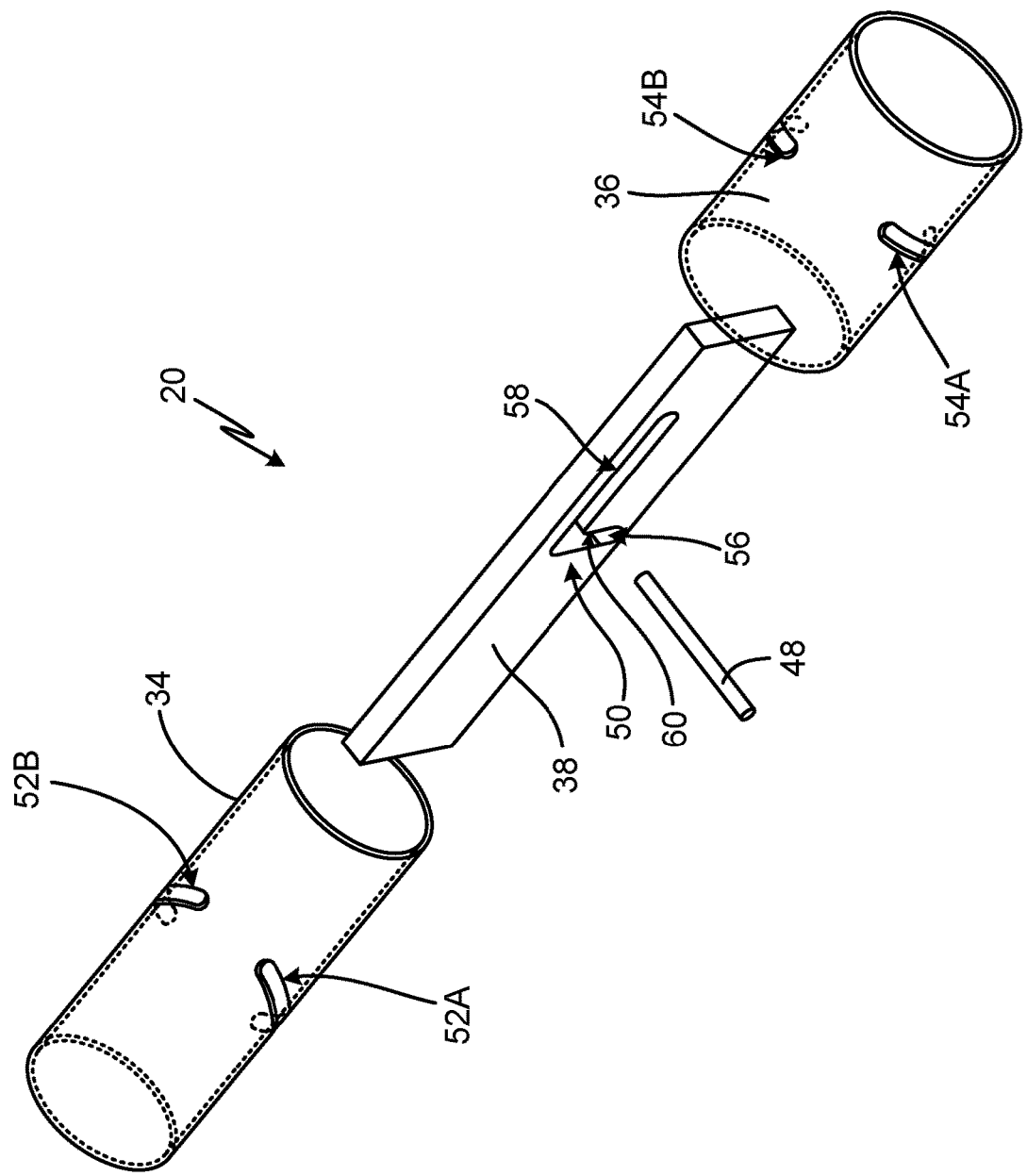
FIG. 2 is an exploded view of the knife blade lockout mechanism showing an inner shaft and outer shaft as transparent.

According to techniques of this disclosure, a forceps includes a knife blade lockout mechanism that prevents deployment of a knife blade to an extended position when jaw members of a gripping assembly are not in a closed configuration. Rather than utilize a direct interaction between control elements of a hand piece of the forceps, such as gripping levers that actuate a gripping assembly and a knife trigger that actuates the knife blade, the knife blade lockout mechanism described herein prevents deployment of the knife blade based on movement of a shaft assembly that directly correlates to open and closed configurations of the jaw members. The knife blade mechanism implementing techniques of this disclosure therefore prevents deployment of the knife blade when the jaw members are not in the closed configuration.

FIG. 1A is a side view of forceps 10. FIG. 1B is a cross-sectional view of portion 1B of forceps 10. For purposes of clarity and ease of discussion, the examples of FIGS. 1A and 1B are described concurrently below.

Forceps 10 can be a medical forceps, cutting forceps, electrosurgical forceps (e.g., monopolar or bipolar forceps), or other types of forceps. Forceps 10, in some examples, is used for medically related procedures, such as open and/or laparoscopic medical procedures to manipulate, engage, grasp, cut, cauterize, seal, or otherwise affect a vessel, tissue, vein, artery, or other anatomical feature or object.

As illustrated in FIG. 1A, forceps 10 includes hand piece 12, shaft assembly 14, knife blade assembly 16, gripping assembly 18, and knife blade lockout mechanism 20. In some examples, such as the illustrated example of FIG. 1A, forceps 10 is electrically connected to power source 22 that supplies electrical energy that is passed through gripping assembly 18 and/or a remote pad for electrosurgical techniques, such as cauterizing, sealing, or other electrosurgical techniques.

Hand piece 12 includes handle 24, gripping lever 26, knife trigger 28, electrical therapy actuation button 30, and rotation wheel 32. Shaft assembly 14 includes inner shaft 34 and outer shaft 36. Knife blade assembly 16 includes blade support 38 and knife blade 40. Gripping assembly 18 includes first jaw member 42 and second jaw member 44. Knife blade lockout mechanism 20, as illustrated in FIG. 1A, can be located within a housing of hand piece 12 and configured to inhibit translation of blade support 38 and knife blade 40 until one or more of first jaw member 42 and second jaw member 44 are moved to a closed configuration, as is further described below. Although illustrated in the example of FIG. 1A as located within the housing of hand piece 12, in other examples, knife blade lockout mechanism 20 can be located at any location along shaft assembly 14.

Shaft assembly 14, including inner shaft 34 and outer shaft 36, extends distally from hand piece 12 in longitudinal direction 46. Outer shaft 36 functions to permit a portion of forceps 10 (e.g., gripping assembly 18 and a portion of shaft assembly 14) to be inserted into a patient or other anatomy while a remaining portion of forceps 10 (e.g., hand piece 12 and a remaining portion of shaft assembly 14) are outside of the patient or other anatomy. Though illustrated in FIG. 1A as substantially straight, in other examples, outer shaft 36 (as well as inner shaft 34 and blade support 38) can include one or more angles, bends, and/or arcs. Outer shaft 36 can be a cylinder with a circular, elliptical, or other cross section, or other elongated member that extends along inner shaft 34 and knife blade assembly 16.

Inner shaft 34, in the example of FIGS. 1A and 1B, is disposed axially within outer shaft 36 and extends in longitudinal direction 46. Inner shaft 34 can be a cylinder, such as a circular or elliptical cylinder, or otherwise elongated member that extends along outer shaft 36 and knife blade assembly 16. In some examples, such as the example of FIGS. 1A and 1B, outer shaft 36 can be an elongated hollow member (e.g., a tubular outer shaft) that encloses inner shaft 34 and knife blade assembly 16. In certain examples, inner shaft 34 can be an elongated hollow member (e.g., a tubular inner shaft) that extends within outer shaft 36 and encloses knife blade assembly 16. In other examples, inner shaft 34 can be an elongated solid member having a circular, rectangular, or other cross section that extends along outer shaft 36 and knife blade assembly 16. In general, inner shaft 34 and outer shaft 36 can be any elongated member having stiffness sufficient to transfer forces along longitudinal direction 46 to cause relative movement of inner shaft 34 and outer shaft 36 in longitudinal direction 46.

Inner shaft 34 and/or outer shaft 36 are connected at a proximal end to hand piece 12, and at a distal end to gripping assembly 18. Relative movement of inner shaft 34 and outer shaft 36 in longitudinal direction 46 causes one or more of first jaw member 42 and second jaw member 44 to move between an open configuration (illustrated in FIG. 1A) in which first jaw member 42 and second jaw member 44 are spaced apart, and a closed configuration in which the gap between first jaw member 42 and second jaw member 44 is reduced or eliminated. For instance, outer shaft 36 can be a stationary (or ground) member relative to hand piece 12, with inner shaft 34 being movable relative to outer shaft 36 to cause one or more of first jaw member 42 and second jaw member 44 to move between the open configuration and the closed configuration. In other examples, inner shaft 34 can be a stationary (or ground) member relative to hand piece 12, with outer shaft 36 being movable relative to inner shaft 34 to cause the movement of first jaw member 42 and/or second jaw member 44 between the open configuration and the closed configuration. In yet other examples, inner shaft 34 and outer shaft 36 can both be movable relative to hand piece 12 (e.g., in opposite directions) to cause first jaw member 42 and second jaw member 44 to move between the open configuration and the closed configuration.

Movement of any one or more of inner shaft 34 and outer shaft 36 can be in a distal direction, a proximal direction, or combinations thereof (e.g., movement of inner shaft 34 in a distal direction and movement of outer shaft 36 in a proximal direction) to cause movement of one or more of first jaw member 42 and second jaw member 44 between the open and closed configurations. One example mechanism for causing movement of a gripping assembly between the open and closed configurations can be found in U.S. Patent Publication No. 2017/0196579, entitled "FORCEPS JAW MECHANISM" and filed on Jan. 10, 2017 to Batchelor et al., the contents of which are hereby incorporated by reference in their entirety.

Knife blade assembly 16, including blade support 38 and knife blade 40, is disposed axially along inner shaft 34 and extends in longitudinal direction 46. Blade support 38 is an elongated rod (or shaft) having a rectangular, circular, elliptical, or other cross section that extends distally from hand piece 12 in longitudinal direction 46 along inner shaft 34. In the example of FIGS. 1A and 1B, blade support 38 extends within inner shaft 34. In other examples, such as when inner shaft 34 is a solid elongated member, blade support 38 can extend along inner shaft 34 (e.g., next to inner shaft 34).

Knife blade 40 is located at a distal end of blade support 38. Blade support 38 is translatable in longitudinal direction 46 along (e.g., within) inner shaft 34 relative to both inner shaft 34 and outer shaft 36 to cause movement of blade support 38 and knife blade 40 between a retracted position (illustrated in FIG. 1A) and a deployed (or extended) position. Knife blade 40, in the deployed position, extends outside both inner shaft 34 and outer shaft 36 and within gripping assembly 18 to cut, excise, or otherwise affect tissue or other object(s) between first jaw member 42 and second jaw member 44.

Hand piece 12, as illustrated in FIG. 1A, includes gripping lever 26, knife trigger 28, therapy actuation button 30, and rotation wheel 32. Movement (e.g., rotation) of rotation wheel 32 causes rotation of one or more of shaft assembly 14, knife blade assembly 16, and gripping assembly 18 about an axis extending in longitudinal direction 46. Actuation of therapy actuation button 30 causes a therapeutic current drawn from, e.g., power source 22, to be applied to one or more of first jaw member 42, second jaw member 44, a remote pad (not illustrated), or other portions of forceps 10 to cauterize, seal, or otherwise electrically affect a patient or other anatomy.

Gripping lever 26 is a gripping actuator that is movable between an open configuration position (illustrated in FIG. 1A) and a closed configuration position in which gripping lever 26 is moved proximally toward handle 24. Movement of gripping lever 26 proximally toward handle 24 to the closed configuration position causes relative movement of inner shaft 34 and outer shaft 36 to transition gripping assembly 18 from the open configuration to the closed configuration. Movement of gripping lever 26 distally (e.g., release of gripping lever 26) causes the relative movement of inner shaft 34 and outer shaft 36 to transition gripping assembly 18 from the closed configuration to the open configuration.

Knife trigger 28 is a knife blade actuator that is movable between a retracted configuration position (illustrated in FIG. 1A) and a deployed (or extended) configuration position in which knife trigger 28 is moved proximally toward handle 24 to deploy knife blade 40. Movement of knife trigger 28 proximally toward handle 24 to the deployed configuration position causes translation of blade support 38 distally in longitudinal direction 46 relative to both inner shaft 34 and outer shaft 36 to the deployed position in which knife blade 40 extends outside both inner shaft 34 and outer shaft 36 within gripping assembly 18. Movement of knife trigger 28 distally (e.g., release of knife trigger 28) causes translation of blade support 38 proximally in longitudinal direction 46 to the retracted position in which knife blade 40 is positioned within inner shaft 34. One example of a hand piece utilizing a gripping lever, knife trigger, rotation wheel, and therapy actuation button can be found in U.S. Pat. No. 9,681,883, entitled "FORCEPS WITH A ROTATION ASSEMBLY" and issued on Jun. 20, 2017 to Windgassen et al., the contents of which are hereby incorporated by reference in their entirety.

According to techniques described herein, knife blade lockout mechanism 20 coordinates movement of a pin through a series of slots formed in inner shaft 34, outer shaft 36, and blade support 38 to prevent distal translation of blade support 38 and knife blade 40 to the deployed position until gripping assembly 18 is in the closed configuration. As is further described below, blade support 38 includes a blade support slot having a locking portion and a guide track portion. Blade support 38 and knife blade 40 are distally translatable relative to inner shaft 34 and outer shaft 36 to the deployed position when the pin extends through the guide track portion of the blade support slot. Distal translation of blade support 38 relative to inner shaft 34 and outer shaft 36 is inhibited when the pin extends through the locking portion of the blade support slot. Cam slots and guide slots formed in inner shaft 34 and outer shaft 36 coordinate movement of the pin from the locking portion of the blade support slot when gripping assembly 18 is not in the closed configuration to the guide track portion of the blade support slot when gripping assembly 18 is in the closed configuration. Accordingly, knife blade lockout mechanism prevents deployment of knife blade 40 when gripping assembly 18 is not in the closed configuration.

FIG. 2 is an exploded view of knife blade lockout mechanism 20 with inner shaft 34 and outer shaft 36 shown as transparent. As illustrated in FIG. 2, knife blade lockout mechanism 20 includes pin 48, blade support slot 50 formed in blade support 38, cam slots 52A and 52B formed in inner shaft 34, and guide slots 54A and 54B formed in outer shaft 36. Blade support slot 50 includes locking portion 56 and guide track portion 58. Locking portion 56 defines engagement shoulder 60.

Though illustrated and described herein as having cam slots 52A-52B formed in inner shaft 34 and guide slots 54A-54B formed in outer shaft 36, it should be understood that in other examples, cam slots 52A-52B can be formed in outer shaft 36 and guide slots 54A-54B can be formed in inner shaft 34. Similarly, though illustrated and described herein as having a pair of cam slots 52A-52B and a pair of guide slots 54A-54B, in other examples, any one or more of inner shaft 34 and outer shaft 36 can include a single cam slot and a single guide slot. For instance, in some examples, inner shaft 34 can include a single cam slot and outer shaft 36 can include a single guide slot. In other examples, inner shaft 34 can include a pair of cam slots (e.g., cam slots 52A-52B) and outer shaft 36 can include a single guide slot (e.g., one of guide slots 54A and 54B). In yet other examples, inner shaft 34 can include a single cam slot (e.g., one of cam slots 52A and 52B) and outer shaft 36 can include a pair of guide slots (e.g., guide slots 54A-54B).

Pin 48 is a pin, shaft, rod, rivet, or other elongated member capable of extending through each of guide slots 54A and 54B, cam slots 52A and 52B, and blade support slot 50. Pin 48 is substantially rigid to prevent distal translation of blade support 38 when pin 48 is located in locking portion 56 of blade support slot 50, as is further described below.

Cam slots 52A and 52B are partial circumferential slots formed in inner shaft 34. Guide slots 54A and 54B are partial circumferential slots formed in outer shaft 36. Cam slot 52A, as illustrated in FIG. 2, is located opposite cam slot 52B relative to a central axis or plane of inner shaft 34. Guide slot 54A is located opposite guide slot 54B relative to a central axis or plane of outer shaft 36.

Figure 3:
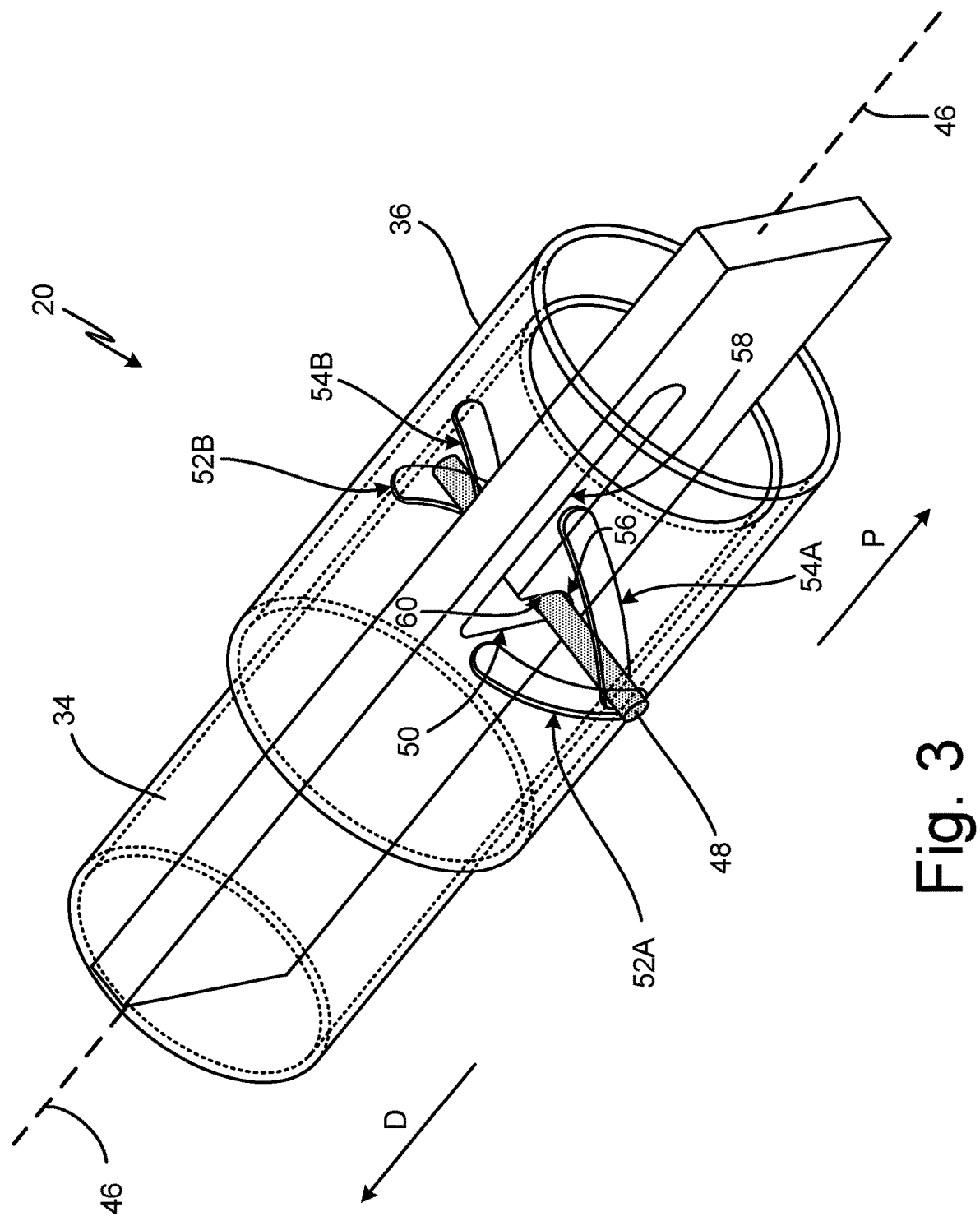
FIG. 3 is an assembled view of the knife blade lockout mechanism showing the inner and outer shafts as transparent.

FIG. 3 is an assembled view of knife blade lockout mechanism 20 with inner shaft 34 and outer shaft 36 shown as transparent. As illustrated in FIG. 3, when assembled, blade support 38 is disposed within inner shaft 34, and inner shaft 34 is disposed axially within outer shaft 36. Blade support slot 50, cam slots 52A and 52B, and guide slots 54A and 54B are aligned such that pin 48 extends through each of blade support slot 50, cam slots 52A and 52B, and guide slots 54A and 54B.

In the example of FIG. 3, pin 48 is located within locking portion 56 of blade support slot 50. That is, the example of FIG. 3 illustrates an assembled state of blade lockout mechanism 20 corresponding to an open configuration of gripping assembly 18 (FIG. 1A). As illustrated, when pin 48 is located in locking portion 56 of blade support slot 50, translation of blade support 38 in distal direction D relative to inner shaft 34 and outer shaft 36 to the extended position is prevented by engagement of pin 48 and engagement shoulder 60. That is, when pin 48 is located in locking portion 56, engagement shoulder 60 contacts pin 48 to prevent translation of blade support 38 in distal direction D relative to inner shaft 34 and outer shaft 36.

As is further described below, during relative movement of inner shaft 34 and outer shaft 36 to move gripping assembly 18 (FIG. 1A) to the closed configuration, cam slots 52A-52B and guide slots 54A-54B coordinate movement of pin 48 from locking portion 56 when gripping assembly 18 is not in the closed configuration (e.g., in the open configuration and during transition to the closed configuration) to guide track portion 58 when gripping assembly 18 is in the closed configuration. Blade support 38 is translatable in distal direction D relative to inner shaft 34 and outer shaft 36 when pin 48 is located in guide track portion 58. That is, blade support 38 is translatable relative to inner shaft 34 and outer shaft 36 in distal direction D to the deployed position and in proximal direction P from the deployed position to the retracted position when pin 48 is located in guide track portion 58. Blade support 38 is not translatable relative to inner shaft 38 in distal direction D (or, in the example of FIG. 3, in proximal direction P) when pin 48 is located in locking portion 56.

Accordingly, locking mechanism 20 inhibits translation of blade support 38 in distal direction D relative to inner shaft 34 and outer shaft 36 when gripping assembly 18 is not in the closed configuration, thereby preventing translation of knife blade 40 (FIG. 1A) to the deployed position until gripping assembly 18 is in the closed configuration.

Figure 4:
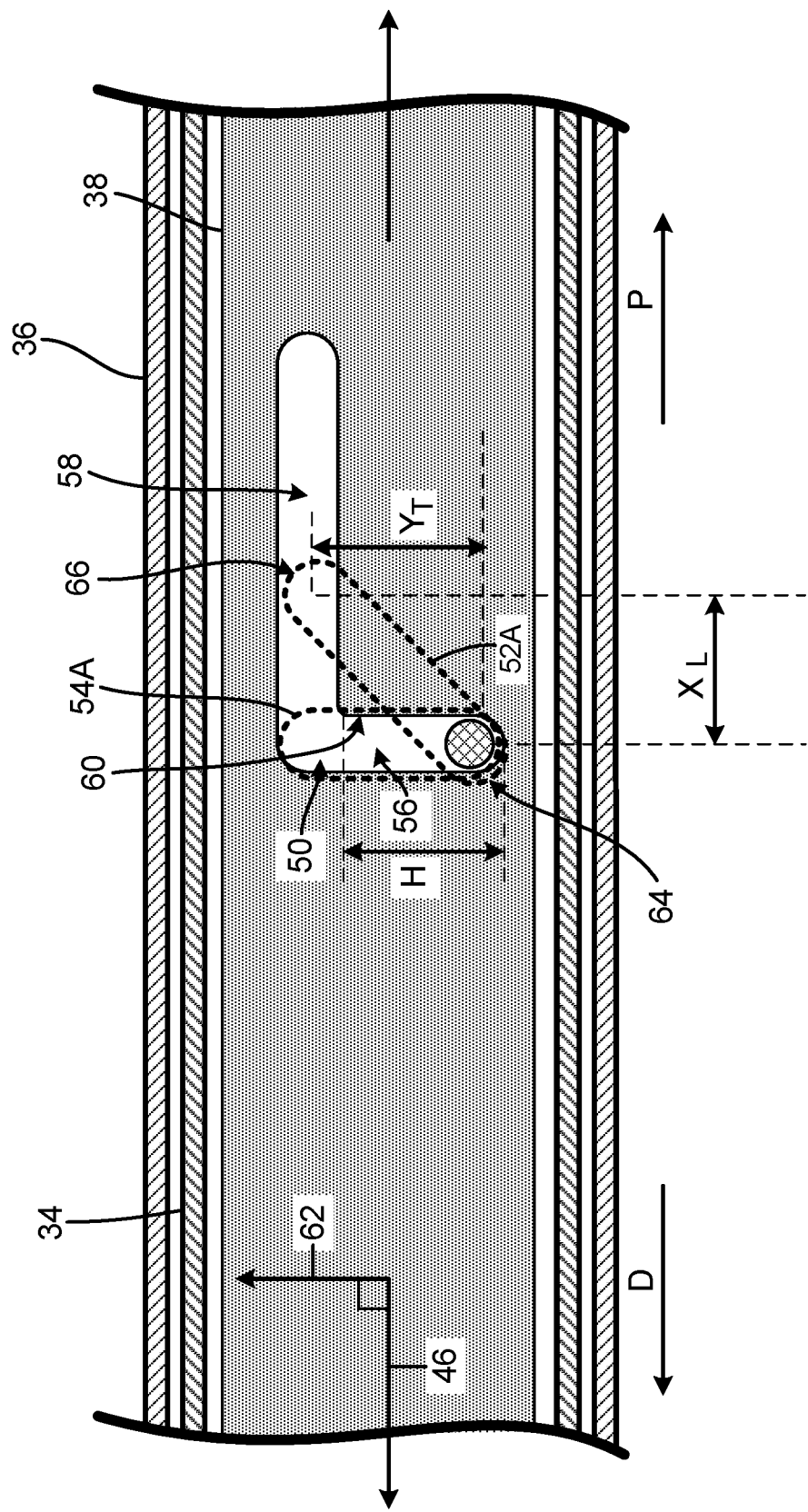
FIG. 4 is a side view of the knife blade lockout mechanism showing the inner and outer shafts as transparent.

FIG. 4 is a side view of locking mechanism 20 showing inner shaft 34 and outer shaft 36 as transparent. The example of FIG. 4 illustrates an assembled state of locking mechanism 20 corresponding to an open configuration of gripping assembly 18 (FIG. 1A) in which pin 48 is located in locking portion 56 of blade support slot 50.

As illustrated in FIG. 4, locking portion 56 of blade support slot 50 extends in transverse direction 62 that is perpendicular to longitudinal direction 46, though transverse direction 62 need not be perpendicular to longitudinal direction 46 in all examples. Guide track portion 58 of blade support slot 50 extends in longitudinal direction 46. Locking portion 56 defines engagement shoulder 60 that extends in transverse direction 62.

In the example of FIG. 4, inner shaft 34 is movable in distal direction D relative to outer shaft 36 to transition gripping assembly 18 from the open configuration to the closed configuration. That is, in the example of FIG. 4, outer shaft 36 is configured as a stationary (or ground) member, and inner shaft 34 is configured to move relative to outer shaft 36 to cause gripping assembly 18 to transition between the open configuration and the closed configuration. In other examples, inner shaft 34 can be configured as a stationary (or ground) member with outer shaft 36 being configured to move relative to inner shaft 36 to cause gripping assembly 18 to transition between the open configuration and the closed configuration. In yet other examples, inner shaft 34 and outer shaft 36 can each be movable (e.g., relative to each other) to cause the transition of gripping assembly 18 between the open configuration and the closed configuration. Similarly, while the example of FIG. 4 utilizes distal movement of inner shaft 34 relative to outer shaft 36, in other examples, either of inner shaft 34 and outer shaft 36 can be movable in proximal direction P to cause gripping assembly 18 to transition between the open configuration and the closed configuration.

In the example of FIG. 4, translation of blade support 38 in distal direction D relative to inner shaft 34 and outer shaft 36 to the deployed position is prevented when pin 48 is located within locking portion 56 of blade support slot 50. That is, physical contact between pin 48 and engagement shoulder 60 prevents movement of blade support 38 in distal direction D relative to inner shaft 34 and outer shaft 36 to the deployed position when pin 48 is located in locking portion 56. Blade support 38 and knife blade 40 (FIG. 1A) are translatable in distal direction D relative to inner shaft 34 and outer shaft 36 from the retracted position (illustrated in FIG. 4) to the deployed position, and in proximal direction P from the deployed position to the retracted position, when pin 48 is located in guide track portion 58 of blade support slot 50.

Cam slots 52A and 52B (cam slot 52B illustrated in FIGS. 2 and 3) and guide slots 54A and 54B (guide slot 54B illustrated in FIGS. 2 and 3) are configured to cause movement of pin 48 within blade support slot 50 from locking portion 56 to guide track portion 58 as inner shaft 34 is translated in distal direction D to cause gripping assembly 18 to transition from the open configuration to the closed configuration. Guide slots 54A and 54B, as illustrated in FIG. 4, extend in transverse direction 62. Cam slots 52A and 52B extend from first position 64 to second position 66, and are angled with respect to both longitudinal direction 46 and transverse direction 62.

As is further described below, as inner shaft 34 is translated in distal direction D (to cause gripping assembly 18 to move to the closed configuration), cam slots 52A and 52B force pin 48 to travel within guide slots 54A and 54B and locking portion 56 in transverse direction 62. Cam slots 52A and 52B are angled to cause pin 48 to be located within locking portion 56 of blade support slot 50 until gripping assembly 18 is in the closed configuration. For example, distance $X_L$ as measured between first position 64 and second position 66 in longitudinal direction 46 can correspond to a distance of relative movement between inner shaft 34 and outer shaft 36 in longitudinal direction 46 to cause gripping assembly 18 to transition between the open configuration and the closed configuration. Distance $X_L$ can be any distance that is greater than or equal to a distance of relative movement between inner shaft 34 and outer shaft 36 in longitudinal direction 46 to cause gripping assembly 18 to transition between the open configuration and the closed configuration. That is, distance $X_L$ is any distance that enables relative movement of inner shaft 34 and outer shaft 36 that is sufficient to transition gripping assembly 18 between the open configuration and the closed configuration.

Distance $Y_T$ as measured between first position 64 and second position 66 in transverse direction 62 can be any distance that is greater than or equal to height H of engagement shoulder 60. For example, distance $Y_T$ can be any distance that causes movement of pin 48 from locking portion 56 in which pin 48 contacts engagement shoulder 60 to guide track portion 58 in which pin 48 does not contact engagement shoulder 60. Accordingly, an angle of cam slots 52A and 52B with respect to longitudinal direction 46 and transverse direction 62 can be defined by distances $X_L$ and $Y_T$, such that translation of inner shaft 34 in distal direction D causes pin 48 to travel within cam slots 52A and 52B from locking portion 56 of blade support slot 50 when gripping assembly 18 is not in the closed configuration to guide track portion 58 of blade support slot 50 when gripping assembly 18 is in the closed configuration.

While the example of FIG. 4 is described above with respect to substantially straight cam slots 52A and 52B, guide slots 54A and 54B, locking portion 56, and guide track portion 58, it should be understood that aspects of this disclosure are not so limited. For instance, in some examples, cam slots 52A and 52B, guide slots 54A and 54B, locking portion 56, and/or guide track portion 58 can be curvilinear having one or more bends, arcs, and/or angles. Similarly, though locking portion 56 and guide track portion 58 are illustrated in FIG. 4 as substantially perpendicular, in other examples, locking portion 56 can be formed at an acute or obtuse angle to guide track portion 58. In general, cam slots 52A and 52B, guide slots 54A and 54B, locking portion 56, and guide track portion 58 are linear and/or curvilinear slots configured to coordinate movement of pin 48 from locking portion 56 when gripping assembly 18 is not in the closed configuration to guide track portion 58 when gripping assembly 18 is in the closed configuration.

Figure 5B:
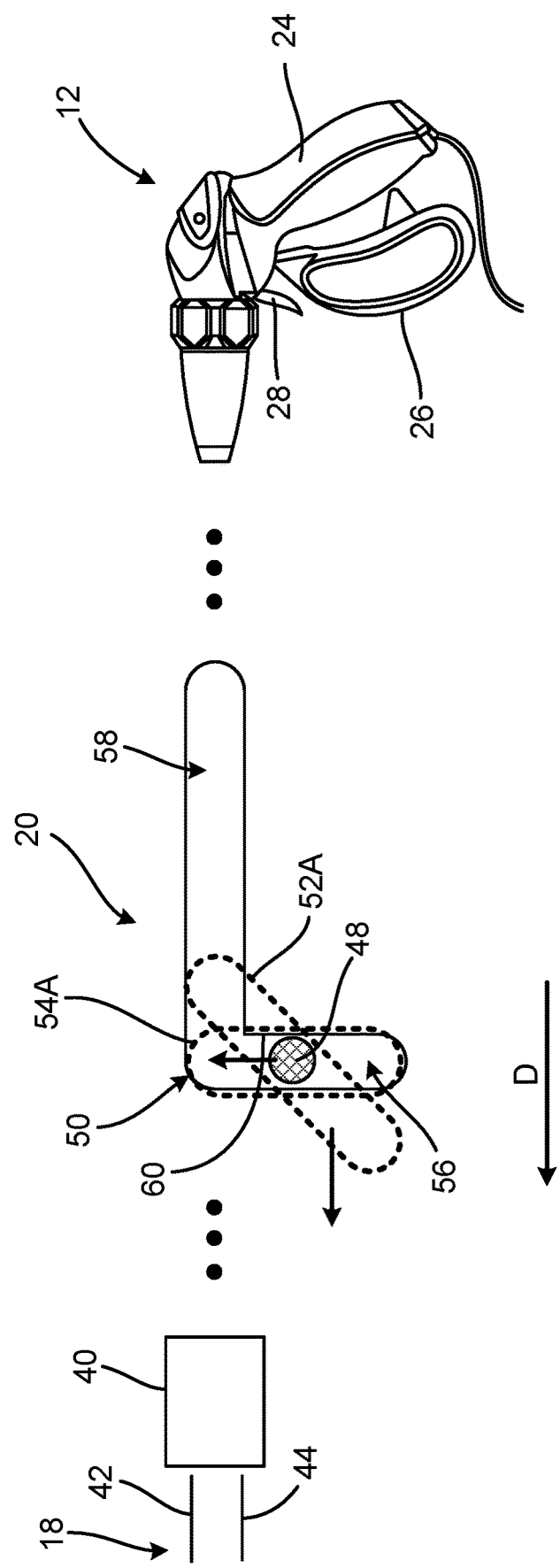
FIG. 5B is a schematic diagram of the forceps showing the hand piece, gripping assembly, and knife blade lockout mechanism when the gripping assembly is transitioning from the open configuration to the closed configuration and the knife blade is retracted.

FIGS. 5A-5D are schematic diagrams illustrating the coordinated movement of pin 48 from locking portion 56 to guide track portion 58 as gripping assembly 18 is transitioned from an open configuration to a closed configuration. FIG. 5A is a schematic diagram illustrating gripping assembly 18, knife blade lockout mechanism 20, and hand piece 12 when gripping assembly 18 is in an open configuration and knife blade 40 is in a retracted position.

As illustrated in FIG. 5A, gripping lever 26 and knife trigger 28 are each extended distally from handle 24, such that gripping lever 26 is in the open configuration position and knife trigger 28 is in the retracted configuration position. Gripping assembly 18 is in the open configuration, such that first jaw member 42 and second jaw member 44 are spaced apart (or open). Knife blade 40 is in the retracted position, such that knife blade 40 does not extend within first jaw member 42 and second jaw member 44 of gripping assembly 18.

In the configuration shown in FIG. 5A, pin 48 extends through each of cam slots 52A and 52B (cam slot 52B illustrated in FIGS. 2 and 3), guide slots 54A and 54B (guide slot 54B illustrated in FIGS. 2 and 3), and locking portion 56 of blade support slot 50. Engagement shoulder 60, in this example, prevents translation of knife blade 40 via blade support 38 (FIGS. 1-4) in distal direction D relative to inner shaft 34 (FIGS. 1-4) and outer shaft 36 (FIGS. 1-4).

FIG. 5B is a schematic diagram illustrating gripping assembly 18, knife blade lockout mechanism 20, and hand piece 12 when gripping assembly 18 is in an open configuration and partially transitioned to the closed configuration. In the example of FIG. 5B, gripping lever 26 is moved proximally toward handle 24. Proximal movement of gripping lever 26 toward handle 24 produces relative movement of inner shaft 34 and outer shaft 36 to cause gripping assembly 18 to transition from the open configuration to the closed configuration, such that first jaw member 42 and second jaw member 44 move toward each other to reduce the gap between first jaw member 42 and second jaw member 44. In the example of FIG. 5B, first jaw member 42 and second jaw member 44 have moved toward each other in transition between the open configuration and the closed configuration, but have not yet reached the closed configuration. Knife trigger 28, in this example, is in the retracted configuration position. Accordingly, knife blade 40 is in the retracted position, such that knife blade 40 does not extend within first jaw member 42 and second jaw member 44 of gripping assembly 18.

As illustrated in FIG. 5B, translation of cam slots 52A-52B in distal direction D relative to guide slots 54A-54B and blade support slot 50 drives pin 48 within guide slots 54A-54B and blade support slot 50 toward guide track portion 58. In this example, gripping assembly 18 is not in the closed configuration, and pin 48 is located within locking portion 56 of blade support slot 50. As such, engagement shoulder 60 prevents translation of knife blade 40 via blade support 38 in distal direction D relative to inner shaft 34 and outer shaft 36.

Figure 5C:
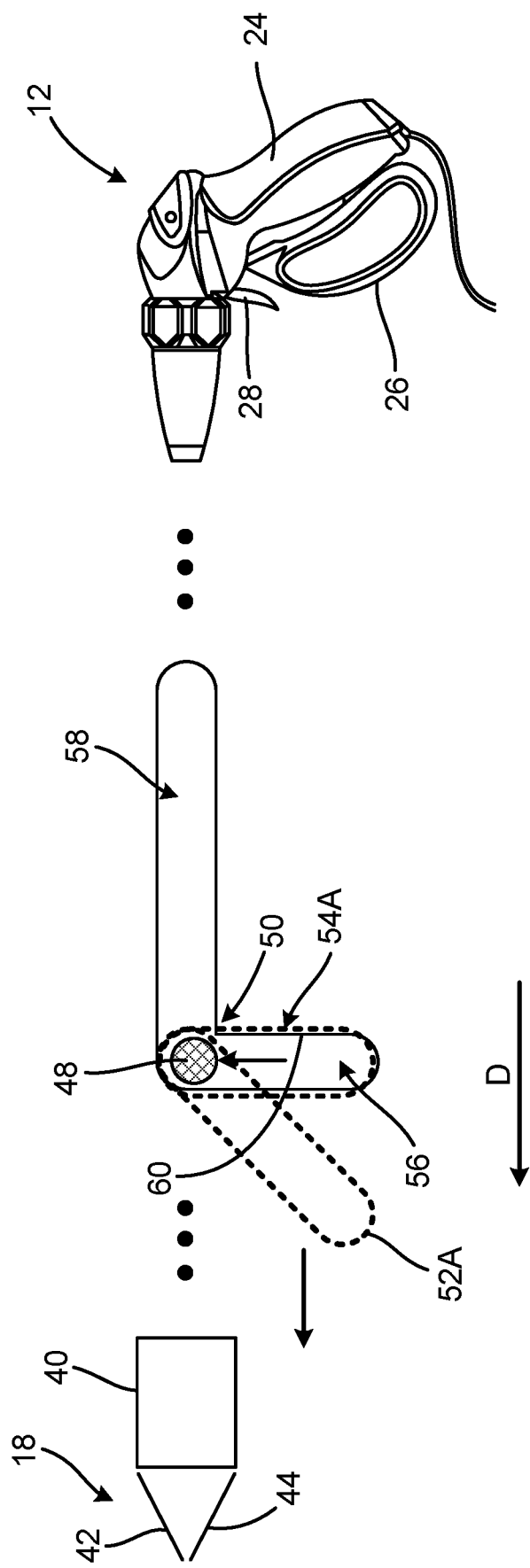
FIG. 5C is a schematic diagram of the forceps showing the hand piece, gripping assembly, and knife blade lockout mechanism when the gripping assembly is in the closed configuration and the knife blade is retracted.

FIG. 5C is a schematic diagram illustrating gripping assembly 18, knife blade lockout mechanism 20, and hand piece 12 when gripping assembly 18 is in a closed configuration and knife blade 40 is in the retracted position. In the example of FIG. 5C, gripping lever 26 is moved proximally toward handle 24 to the closed configuration position. Proximal movement of gripping lever 26 toward handle 24 produces relative movement of inner shaft 34 and outer shaft 36 to cause gripping assembly 18 to transition from the open configuration towards the closed configuration, such that first jaw member 42 and second jaw member 44 move toward each other to reduce or eliminate the gap between first jaw member 42 and second jaw member 44. Knife trigger 28, in this example, is in the retracted configuration position. Accordingly, knife blade 40 is in the retracted position, such that knife blade 40 does not extend within first jaw member 42 and second jaw member 44 of gripping assembly 18.

In the example of FIG. 5C, translation of cam slots 52A-52B in distal direction D relative to guide slots 54A-54B and blade support slot 50 drives pin 48 within guide slots 54A-54B and blade support slot 50 to guide track portion 58. That is, in the example of FIG. 5C, pin 48 is located in guide track portion 58 of blade support slot 50. As such, engagement shoulder 60 no longer prevents translation of knife blade 40 via blade support 38 in distal direction D relative to inner shaft 34 and outer shaft 36. Blade support 38 is therefore movable by actuation of knife trigger 28 to translate distally relative to inner shaft 34 and outer shaft 36 to the deployed position.

Figure 5D:
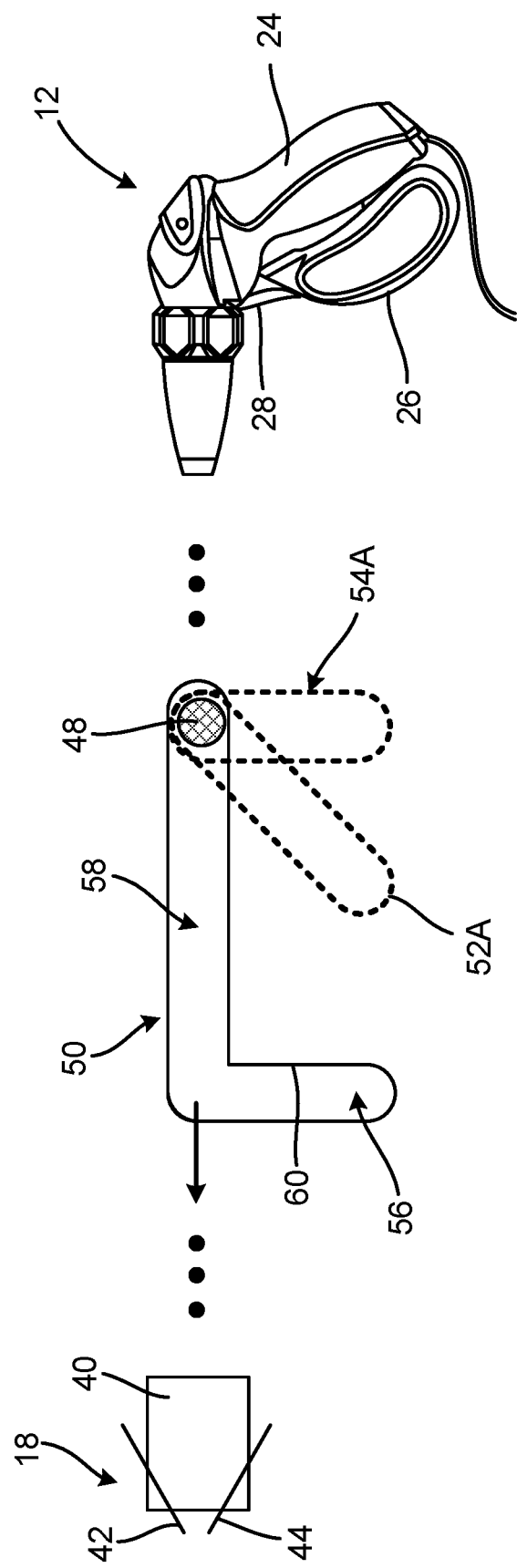
FIG. 5D is a schematic diagram of the forceps showing the hand piece, gripping assembly, and knife blade lockout mechanism when the gripping assembly is in the closed configuration and the knife blade is extended.

FIG. 5D is a schematic diagram illustrating gripping assembly 18, knife blade lockout mechanism 20, and hand piece 12 when gripping assembly 18 is in the closed configuration and knife blade 40 is in the deployed position. In the example of FIG. 5D, gripping lever 26 is moved proximally toward handle 24 to the closed configuration position. In addition, knife trigger 28 is moved proximally toward handle 24 to the deployed configuration position. Proximal movement of knife trigger 28 produces movement of blade support 38 relative to both inner shaft 34 and outer shaft 36 in distal direction D to the deployed position. Accordingly, as illustrated in FIG. 5D, knife blade 40 is translated in distal direction D within first jaw member 42 and second jaw member 44 of gripping assembly 18 to the deployed position to cut or dissect tissue or other anatomy held between first jaw member 42 and second jaw member 44.

In operation, distal movement (e.g., release) of knife trigger 28 and distal movement (e.g., release) of gripping lever 26 reverse the operations of FIGS. 5A-5D to transition gripping assembly 18 to the open configuration and move pin 48 from guide track portion 58 to locking portion 56. That is, distal movement of knife trigger 28 to the retracted configuration position produces reversed movement of blade support 38 (i.e., in a proximal direction opposite distal direction D) relative to both inner shaft 34 and outer shaft 36 to the retracted configuration position. Distal movement of gripping lever 26 produces reversed relative motion of inner shaft 34 and outer shaft 36 to transition gripping assembly 18 to the open configuration and move pin 48 from guide track portion 58 to locking portion 56.

Accordingly, knife blade lockout mechanism 20 prevents deployment of knife blade 40 to an extended position when first jaw member 42 and second jaw member 44 of gripping assembly 18 are not in a closed configuration. Coordinated movement of pin 48 through cam slots 52A-52B, guide slots 54A-54B, and blade support slot 50 as the relative movement of inner shaft 34 and outer shaft 36 causes gripping assembly 18 to transition between the open configuration and the closed configuration prevents distal translation of knife blade 40 to the deployed position until gripping assembly 18 is in the closed configuration.

Discussion of Possible Embodiments

The following are non-exclusive descriptions of possible embodiments of the present invention.

A forceps includes jaws that open and close, a first shaft, a second shaft, a rod, a pin, a first actuator, and a second actuator. The first shaft has a first slot. The second shaft extends along the first shaft and has a second slot. The first slot and the second slot are angled with respect to each other. The rod extends along the second shaft and has a third slot including a locking portion and a guide track portion. The pin extends through the first slot, the second slot, and the third slot to prevent deployment of the rod when the pin is located in the locking portion of the third slot and to permit deployment of the rod when the pin is located in the guide track portion of the third slot. The first actuator produces relative movement of the first shaft and the second shaft to move the jaws relative to each other and move the pin within the first slot and the second slot from the locking portion to the guide track portion of the third slot. The second actuator produces movement of the rod to deploy the rod when the pin is located in the guide track portion.

The forceps of the preceding paragraph can optionally include, additionally and/or alternatively, any one or more of the following features, configurations, operations, and/or additional components:

The first shaft can be a tubular outer shaft.

The second shaft can be a tubular inner shaft extending within the tubular outer shaft.

The rod can be a blade support that extends within the inner shaft.

A knife blade can be connected to a distal end of the rod.

The knife blade can be positioned to extend outside each of the first shaft and the second shaft when the rod is deployed.

The knife blade can be configured to extend within the jaws when the jaws are closed and the rod is deployed.

The first actuator can produce the relative movement of the first shaft and the second shaft to move the pin within the first slot and the second slot from the locking portion to the guide track portion of the third slot as the jaws move toward a closed configuration.

The first actuator can be a gripping actuator.

The first actuator can produce the relative movement of the first shaft and the second shaft to move the pin from the locking portion to the guide track portion of the third slot as the jaws move toward the closed configured when the first actuator is moved in a first direction. The first actuator can reverse the relative movement of the first shaft and the second shaft to move the pin from the guide track portion to the locking portion of the third slot when the first actuator is moved in a second direction.

The first direction can be a proximal direction. The second direction can be a distal direction.

The second actuator can be a knife blade actuator.

The second actuator can produce the movement of the rod to deploy the rod when the pin is located in the guide track portion of the third slot and the second actuator is moved in a first direction. The second actuator can reverse the movement of the rod to retract the rod when the pin is located in the guide track portion of the third slot and the second actuator is moved in a second direction.

The first direction can be a proximal direction. The second direction can be a distal direction.

The first shaft can include a fourth slot opposite the first slot. The second shaft can include a fifth slot opposite the second slot. The pin can extend through the first slot, the second slot, the third slot, the fourth slot, and the fifth slot. The first actuator can produce the relative movement of the first shaft and the second shaft to move the jaws relative to each other and move the pin within the first slot, the second slot, the fourth slot, and the fifth slot between the locking portion and the guide track portion of the third slot.

The guide track portion of the third slot can extend in a longitudinal direction. The locking portion of the third slot can extend in a transverse direction.

The longitudinal direction and the transverse direction can be perpendicular.

The first slot can be a guide slot. The second slot can be a cam slot.

Each of the guide slot and the cam slot can be substantially straight.

The guide slot can extend in the transverse direction.

The cam slot can be angled with respect to each of the longitudinal direction and the transverse direction.

The second slot can extend from a first position to a second position. A distance between the first position and the second position in the longitudinal direction can be greater than or equal to a distance of relative movement of the first shaft and the second shaft in the longitudinal direction to open and close the jaws.

A length of the guide track portion of the third slot in the longitudinal direction can be greater than or equal to a distance of movement of the rod in the longitudinal direction to deploy the rod.

The locking portion of the third slot can define an engagement shoulder that contacts the pin when the pin is located in the locking portion of the third slot to prevent deployment of the rod.

A method includes producing relative movement of a first shaft and a second shaft to move jaws of a forceps towards a closed configuration. The method further includes moving, during the relative movement of the first shaft and the second shaft, a pin that extends through a first slot in the inner shaft, a second slot in the outer shaft, and a third slot of a rod from a locking portion of the third slot to a guide track portion of the third slot. The method further includes producing movement of the rod relative to the first shaft and the second shaft to deploy the rod when the pin is located in the guide track portion of the third slot.

The method of the preceding paragraph can optionally include, additionally and/or alternatively, any one or more of the following features, configurations, operations, and/or additional components:

The first shaft can be a tubular outer shaft.

The second shaft can be a tubular inner shaft extending within the tubular outer shaft.

The rod can be a blade support extending within the tubular inner shaft.

Producing the movement of the rod relative to the first shaft and the second shaft to deploy the rod can include producing the movement of the rod relative to the first shaft and the second shaft to deploy a knife blade connected to a distal end of the rod.

Producing the movement of the rod relative to the first shaft and the second shaft to deploy the knife blade can include producing the movement of the rod relative to the first shaft and the second shaft to deploy the knife blade outside each of the first shaft and the second shaft.

Producing the movement of the rod relative to the first shaft and the second shaft to deploy the knife blade outside each of the first shaft and the second shaft can include producing the movement of the rod relative to the first shaft and the second shaft to deploy the knife blade outside each of the first shaft and the second shaft and to extend within the jaws.

Moving, during the relative movement of the first shaft and the second shaft, the pin that extends through the first slot in the first shaft, the second slot in the second shaft, and the third slot of a rod from the locking portion of the third slot to the guide track portion of the third slot can include moving, during the relative movement of the first shaft and the second shaft, the pin that extends through the first slot in the first shaft, the second slot in the second shaft, the third slot of the rod, a fourth slot in the first shaft opposite the first slot, and a fifth slot in the second shaft opposite the second slot.

The third slot can prevent deployment of the rod when the pin is in the locking portion of the third slot.

The method can further include reversing the movement of the rod relative to the first shaft and the second shaft to retract the rod when the pin is located in the guide track portion of the third slot.

The method can further include moving, while reversing the relative movement of the first shaft and the second shaft, the pin from the guide track portion of the third slot to the locking portion of the third slot.

Producing the relative movement of the first shaft and the second shaft to move the jaws of the forceps toward the closed configuration can include producing the relative movement of the first shaft and the second shaft in a longitudinal direction. Moving the pin from the locking portion of the third slot to the guide track portion of the third slot can include moving the pin in a direction that is transverse to the longitudinal direction.

The direction that is transverse to the longitudinal direction can be perpendicular to the longitudinal direction.

Producing the movement of the rod relative to the first shaft and the second shaft to deploy the rod can include producing the movement of the rod relative to the first shaft and the second shaft in the longitudinal direction.

A forceps includes a shaft assembly, a gripping assembly, a knife blade assembly, a knife blade lockout mechanism, a gripping actuator, and a knife blade actuator. The shaft assembly has a first shaft and a second shaft. The gripping assembly is operably coupled to a distal end of the shaft assembly and includes a first jaw member and a second jaw member. The knife blade assembly includes a blade support and a knife blade. The blade support extends longitudinally within the shaft assembly. The knife blade is connected to a distal end of the blade support. The knife blade lockout mechanism includes guide slots, cam slots, a blade support slot, and a pin. The guide slots are formed in the first shaft. The cam slots are formed in the second shaft. The blade support slot is formed in the blade support. The blade support slot has a locking portion and a guide track portion. The pin extends through the guide slots, the cam slots, and the blade support slot to prevent distal translation of the blade support and the knife blade when the pin is located in the locking portion and to allow distal translation of the blade support and the knife blade when the pin is located in the guide track portion. The gripping actuator is operably connected to the shaft assembly to produce relative movement of the first shaft and the second shaft that causes at least one of the first jaw member and the second jaw member to transition from an open configuration to a closed configuration and causes the guide slots and the cam slots to move the pin from the locking portion to the guide track portion of the blade support slot. The knife blade actuator is operably connected to the knife blade assembly to produce distal translation of the blade support relative to the first shaft and the second shaft to extend the knife blade when the pin is located in the guide track portion of the blade support slot.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:
1. A forceps comprising:
jaws that open and close;
a first shaft having a first slot;
a second shaft extending along the first shaft, the second shaft having a second slot, wherein the first slot and the second slot are angled with respect to each other;
a rod that extends along the second shaft, the rod having a third slot including a locking portion and a guide track portion;
a pin that extends through the first slot, the second slot, and the third slot to prevent deployment of the rod when the pin is located in the locking portion of the third slot and to permit deployment of the rod when the pin is located in the guide track portion of the third slot;
a first actuator that produces relative movement of the first shaft and the second shaft to move the jaws relative to each other and move the pin within the first slot and the second slot between the locking portion and the guide track portion of the third slot; and
a second actuator that produces movement of the rod to deploy the rod when the pin is located in the guide track portion;
wherein the first shaft is a tubular outer shaft and the first slot is formed within a tubular wall of the tubular outer shaft;

wherein the second shaft is a tubular inner shaft extending within the tubular outer shaft and the second slot is formed within a tubular wall of the tubular inner shaft; and wherein the rod is a blade support that extends within the inner shaft.

2. The forceps of claim 1, further comprising:
a knife blade connected to a distal end of the rod.

3. The forceps of claim 1,
wherein the first actuator produces the relative movement of the first shaft and the second shaft to move the pin within the first slot and the second slot from the locking portion to the guide track portion of the third slot as the jaws move toward a closed configuration.

4. The forceps of claim 3,
wherein the first actuator produces the relative movement of the first shaft and the second shaft to move the pin from the locking portion to the guide track portion of the third slot as the jaws move toward the closed configuration when the first actuator is moved in a first direction; and
wherein the first actuator reverses the relative movement of the first shaft and the second shaft to move the pin from the guide track portion to the locking portion of the third slot when the first actuator is moved in a second direction.

5. The forceps of claim 1,
wherein the second actuator produces the movement of the rod to deploy the rod when the pin is located in the guide track portion of the third slot and the second actuator is moved in a first direction; and
wherein the second actuator reverses the movement of the rod to retract the rod when the pin is located in the guide track portion of the third slot and the second actuator is moved in a second direction.

6. The forceps of claim 1,
wherein the first shaft has a fourth slot opposite the first slot;
wherein the second shaft has a fifth slot opposite the second slot;
wherein the pin extends through the first slot, the second slot, the third slot, the fourth slot, and the fifth slot; and
wherein the first actuator produces the relative movement of the first shaft and the second shaft to move the jaws relative to each other and move the pin within the first slot, the second slot, the fourth slot, and the fifth slot between the locking portion and the guide track portion of the third slot.

7. The forceps of claim 1,
wherein the guide track portion of the third slot extends in a longitudinal direction; and
wherein the locking portion of the third slot extends in a transverse direction.

8. The forceps of claim 7,
wherein the first slot extends in the transverse direction; and
wherein the second slot is angled with respect to each of the longitudinal direction and the transverse direction.

9. The forceps of claim 1,
wherein each of the first slot and the second slot are substantially straight.

10. The forceps of claim 1,
wherein the locking portion of the third slot defines an engagement shoulder that contacts the pin when the pin is located in the locking portion of the third slot to prevent deployment of the rod.

11. A method comprising:
producing relative movement of a first shaft and a second shaft to move jaws of a forceps toward a closed configuration;
moving, during the relative movement of the first shaft and the second shaft, a pin that extends through a first slot in the first shaft, a second slot in the second shaft, and a third slot of a rod from a locking portion of the third slot to a guide track portion of the third slot;
producing movement of the rod relative to the first shaft and the second shaft to deploy the rod when the pin is located in the guide track portion of the third slot; and
reversing the movement of the rod relative to the first shaft and the second shaft to retract the rod when the pin is located in the guide track portion of the third slot.

12. The method of claim 11,
wherein the first shaft is a tubular outer shaft;
wherein the second shaft is a tubular inner shaft extending within the tubular outer shaft; and
wherein the rod is a blade support extending within the tubular inner shaft.

13. The method of claim 11,
wherein producing the movement of the rod relative to the first shaft and the second shaft to deploy the rod comprises producing the movement of the rod relative to the first shaft and the second shaft to deploy a knife blade connected to a distal end of the rod.

14. The method of claim 11,
wherein the third slot prevents deployment of the rod when the pin is in the locking portion of the third slot.

15. The method of claim 11, further comprising:
reversing the relative movement of the first shaft and the second shaft to move the jaws of the forceps toward an open configuration.

16. The method of claim 15, further comprising:
moving, while reversing the relative movement of the first shaft and the second shaft, the pin from the guide track portion of the third slot to the locking portion of the third slot.

17. The method of claim 11,
wherein producing the relative movement of the first shaft and the second shaft to move the jaws of the forceps toward the closed configuration comprises producing the relative movement of the first shaft and the second shaft in a longitudinal direction; and
wherein moving the pin from the locking portion of the third slot to the guide track portion of the third slot comprises moving the pin in a direction that is transverse to the longitudinal direction.

18. A forceps comprising:
a shaft assembly having a first shaft and a second shaft;
a gripping assembly operably coupled to a distal end of the shaft assembly and including a first jaw member and a second jaw member;
a knife blade assembly comprising:
  a blade support extending longitudinally within the shaft assembly; and
  a knife blade connected to a distal end of the blade support;
a knife blade lockout mechanism comprising:
  guide slots formed in the first shaft and a pin slidably received in the guide slots;
  cam slots formed in the second shaft;
  a blade support slot formed in the blade support, the blade support slot having a locking portion and a guide track portion; and the pin extending through the guide slots, the cam slots, and the blade support slot to prevent distal translation of the blade support and the knife blade when the pin is located in the locking portion and to allow distal translation of the blade support and the knife blade when the pin is located in the guide track portion;

a gripping actuator operably connected to the shaft assembly to produce relative movement of the first shaft and the second shaft that causes at least one of the first jaw member and the second jaw member to transition from an open configuration to a closed configuration and causes the guide slots and the cam slots to move the pin from the locking portion to the guide track portion of the blade support slot; and a knife blade actuator operably connected to the knife blade assembly to produce distal translation of the blade support relative to the first shaft and the second shaft to extend the knife blade when the pin is located in the guide track portion of the blade support slot, and to produce proximal translation of the blade support relative to the first shaft and the second shaft to retract the knife blade when the pin is located in the guide track portion of the blade support slot.

\* \* \* \* \*